United States Patent [19]
Ellis

[11] 3,932,444
[45] Jan. 13, 1976

[54] 4-IMIDAZOLYLSULFONYLIMIDAZOLES
[75] Inventor: Richard Lee Ellis, Wilmington, Del.
[73] Assignee: E. I. Du Pont de Nemours & Co., Wilmington, Del.
[22] Filed: Feb. 26, 1974
[21] Appl. No.: 445,913

Related U.S. Application Data

[63] Continuation-in-part of Ser. No. 248,596, April 28, 1972, abandoned.

[52] U.S. Cl............ 260/309; 260/30.2; 260/30.8 R; 260/247.1 M; 260/288 R; 260/293.7; 260/294.8 F; 260/306.7; 260/306.8 D; 260/308 R; 260/309.2; 260/309.7; 260/310 R; 252/8.1; 428/921
[51] Int. Cl.² ........................................ C07D 233/84
[58] Field of Search ..................... 260/309, 309.2

[56] References Cited
UNITED STATES PATENTS
2,603,649  7/1952  Clapp et al. ................. 260/309

OTHER PUBLICATIONS
Staab et al., C.A. 65 : 12195–12196 (1966).
Walter et al., C.A. 73 : 120553m, (1970).

Primary Examiner—Sherman D. Winters

[57] ABSTRACT

4-Imidazolylsulfonamides and 4-imidazolylsulfonylimidazoles are useful as plasticizers. These compounds are obtained by reaction of 4-imidazolesulfonyl chloride with an amine, such as imidazole. 4-Imidazolesulfonyl chloride itself is useful as a reactant with textile materials such as cotton to increase flame resistance.

8 Claims, No Drawings

4-IMIDAZOLYLSULFONYLIMIDAZOLES

CROSS REFERENCE TO RELATED APPLICATION

This application is a continuation-in-part of my copending application Ser. No. 248,596, filed Apr. 28, 1972, and now abandoned.

BACKGROUND OF THE INVENTION

1. Field of the Invention

This invention relates to novel 4-imidazolylsulfonyl chloride and its reaction products with amines having hydrogen on nitrogen which products are effective as plasticizers for chlorine containing polymers.

2. Description of the Prior Art

2-Imidazolesulfonyl chloride preparation and its reaction with ammonia or alkyl or aryl amines has been shown in U.S. Pat. No. 2,603,649. The amides are stated to be carbonic anhydrase inhibitors. The process for 2-imidazolesulfonyl chloride cannot be used to give the 4-isomer.

SUMMARY OF THE INVENTION

The invention is a compound having the general formula

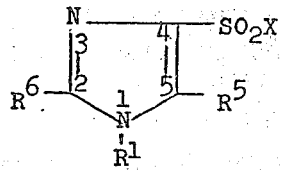

wherein
X is

in which
$R^1$ is H, alkyl of 1–3 carbons, alkenyl of 3 carbons, aminocarbonyl or alkylaminocarbonyl in which the alkyl group is methyl, benzoyl; aralkyl of 7 to 19 carbons; alkanoyl of up to 7 carbons; benzoylmethyl or cycloalkanoyl of 4 carbons;
$R^5$ and $R^6$ individually are H or alkyl of 1–3 carbons;
$R^7$ and $R^8$ individually are H, alkyl, cycloalkyl, alkenyl, aryl, alkaryl, aralkyl, arylguanyl or heterocycle of 5 or 6 ring atoms with up to two nitrogen or oxygen atoms, each of up to 8 carbons, any substituent on an aryl group being cyano or carbonyl; and together $R^7$ and $R^8$ are a heterocyclic ring of 5–7 atoms of which no more than 3 of the ring carbons are replaced by oxygen, nitrogen or sulfur, any substituent on the heterocyclic ring being alkyl of 1–17 carbons, alkenyl of up to 3 carbons, thioalkyl of up to 2 carbons, carbamoyl, carboxyl, carbonyl, aryl of up to 12 carbons, or such aryl having up to 2 halo, nitro, amino, alkyl or alkenyl each of up to 3 carbons.

Presently preferred are the compounds where $R^7$ and $R^8$ together have the structure

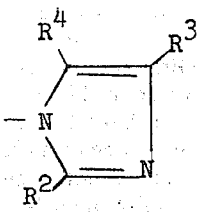

wherein,
$R^2$, $R^3$, and $R^4$ individually are H; alkyl of up to 17 carbons; cycloalkyl of up to 6 carbons; aryl of 6–12 carbons; aryl substituted with up to two alkyl, halo, nitro, amino or methoxy groups; alkenyl of 3 carbons; carbalkoxyalkyl or carbalkoxyalkenyl each carbons; thioalkyl of 1–2 carbons; with the proviso that $R^3$ and $R^4$ together can be a divalent hydrocarbyl group of 4 chain carbons and having a total of from 4 to 8 carbons.

Particularly preferred are the compounds where $R^2$, $R^3$ and $R^4$ are alkyl of 1 to 4 carbons.

The compounds are prepared by reacting 4-imidazolylsulfonyl chloride with an amine compound $HNR^7R^8$ where the groups are as previously stated. The preferred compounds are prepared where $HNR^7R^8$ has the formula

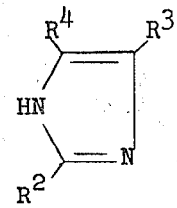

4-Imidazolylsulfonyl chloride has not been heretofore described. The first step in its preparation is reaction between chlorosulfonic acid and imidazole (or an imidazole having hydrocarbyl substituent on nitrogen). This should be run under nitrogen atmosphere to give best yields and highest purity. The reaction temperature is preferably 140°–150°C. At lower temperatures the reaction gives lower yields while higher temperatures cause charring. The second step involves refluxing with a molar amount of thionyl chloride and the reflux period should be of such duration as to completely consume all of the latter. A short reflux time results in lower yields. Long reflux periods (up to 16 hours at 100°) are satisfactory.

An alternative but less preferred route converts imidazole-4-sulfonic acid to its sodium, potassium or barium salt. Treatment of the salt with phosphorus pentachloride gives the imidazole-4-sulfonyl chloride.

The imidazoles which are reacted with the 4-imidazolylsulfonyl chloride are generally readily available. Processes that can be used for preparation of suitable imidazoles having a substituent have been described by combining the procedure of E. L. Brown, N. Campbell, J. Chem. Soc., 1937, 1699 with East German Pat. No. 73,768 (1970), and with "Chemistry of Heterocyclic Compounds, Imidazole and its Derivatives," K. Hofmann, Ed., page 42, Interscience Publishers, New York, 1953. A further procedure is described by J. K. Lawson, Jr., J. Am. Chem. Soc., 75, 3398 (1953), while M. L. Scheinbaum and M. B. Dines, Tetrahedron Let., No. 24, 2205 (1971) show the preparation of 2-,4-, and or 5-substituted imidazoles.

Several 2-substituted, 2,4-disubstituted and 2,4,5-trisubstituted imidazoles are commercially available, e.g., 2-methylimidazole, 2-ethylimidazole, 2-n- propylimidazole, 2-ethyl-4-methylimidazole, 4,5-diphenylimidazole, and 2-methyl-4,5-diphenylimidazole. Other mono-, di- and tri-substituted imidazoles are known or readily available by the processes described above. Useful imidazoles having hydrocarbyl substituents on one or more carbons include the following: 4-allyl-5-methylimidazole, 2-benzylimidazole, 2-benzyl-4-methyl-5-phenylimidazole, 4,5-bis(p-methylphenyl)-imidazole, 4,5-dimethyl-2-phenylimidazole, 4,5diphenyl-2-isopropylimidazole, 2-heptylimidazole, tetrahydrobenzimidazole, 2-cyclohexylimidazole, and 2-cyclopropylimidazole.

The reaction is preferably conducted at 20°–100°C. for times of from a few minutes to several days. Preferably an inert solvent or diluent, such as tetrahydrofuran, is present. Other solvents include acetone or methyl propyl ketone. In the reaction, two equivalents of the second imidazole per equivalent of imidazole-4-sulfonyl chloride has been found to give superior yields.

The product of the reaction of 2-imidazole-4-sulfonyl chloride with an imidazole as described above has the structure

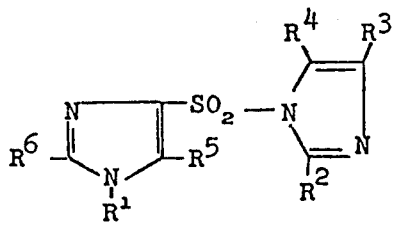

wherein $R^1$ is hydrogen and the other R groups are as previously stated. These compounds can be alkylated or acylated to replace hydrogen by hydrocarbyl, acyl, aroyl or hydroxyalkyl of preferably up to 7 carbons. For example, reaction of 1-(4-imidazolylsulfonyl)-2-methylimidazole with an alkyl halide such as propyl bromide in the presence of sodium hydride in dimethylformamide gives 1-(1-propyl-4-imidazolylsulfonyl)-2-methylimidazole.

SPECIFIC EMBODIMENTS OF THE INVENTION

In the following illustrative examples all parts are by weight and all temperatures are in °C. unless otherwise stated.

EXAMPLE 1

1-(4-IMIDAZOLYLSULFONYL)IMIDAZOLE $R^1 = R^2 = R^3 = R^4 = R^5 = R^6 = H$ a. Three hundred ml of chlorosulfonic acid was added to a flame-dried 2 liter four-neck flask equipped with a reflux condenser, mechanical stirrer, thermometer and nitrogen gas inlet and 100 g of imidazole was added in small portions over a one hour period with stirring under nitrogen at 40°C.± 5°. When the addition was complete the reaction mixture was heated at 140° for 16 hours with stirring. The reaction mixture was cooled to 40° and 107 ml of thionyl chloride added from an addition funnel with stirring. When the addition was complete the mixture was heated to reflux. The reflux began at about 80° and slowly rose to 105°–110° over a six hour period when the refluxing ceased. The clear reaction mixture was cooled to 25° and poured slowly with stirring onto 1.5 kg of cracked ice containing 100 g of sodium chloride. The crude white product was filtered when all the ice had melted, rinsed with ice cold water and dried under vacuum over NaOH. The yield of crude, dry product was 67% (average) with mp 177°–79°. The imidazole-4-sulfonylchloride when recrystallized from ethyl acetate as white plates had mp 179°–81°, $\lambda_{max}^{nujol}$ 3.12 (NH), 6.18 (C=C), 7.30 (SO$_2$Cl) and 8.12 μ (SO$_2$Cl).

Anal. Calcd for C$_3$H$_3$N$_2$O$_2$SCl: C, 21.62; H, 1.81; N, 16.82. Found: C, 21.77; H, 1.95; N, 16.51.

b. A dry round botton flask equipped with a magnetic stirrer, reflux condenser and nitrogen inlet was charged with a filtered solution of 8.33 g of imidazole-4-sulfonylchloride in 300 ml of tetrahydrofuran (THF). The clear solution was treated with 7.0 g of imidazole in one portion and allowed to stir overnight at room temperature. The reaction mixture was filtered and the filtrate concentrated to dryness. All the solids were triturated with water, filtered, rinsed with water and dried at high vacuum over NaOH. Recrystallization from ethanol gave 5.35 g of white crystals of 1-(4-imidazolylsulfonyl)imidazole mp 208°–10°, $\lambda_{max}^{nujol}$ 3.21 (HH), 7.29 (SO$_2$N) and 8.52 μ (SO$_2$N). NMR (DMSO, d$_6$) 570–510 Hz, M, 1H; 497 Hz, t, J ~ 1 Hz, 2H; 481 Hz, d J ~ 1 Hz, 1H; 457 Hz, t, J ~ 1 Hz, 1H; 429 Hz, t, J ~ 1 Hz, 1 H.

Anal. Calcd. for C$_6$H$_6$N$_4$SO$_2$: C, 36.36; H, 3.05; N, 28.28. Found: C, 36.59; H, 2.79; N, 28.09.

EXAMPLE 2

1-(4-IMIDAZOLYLSULFONYL)-2-METHYLIMIDAZOLE $R^1 = R^3 = R^4 = R^5 = R^6 = H$
$R^2 = CH_3$

A dry round bottom flask equipped with a magnetic stirrer, reflux condenser and nitrogen inlet was charged with a filtered solution of 8.33 g of imidazole-4-sulfonylchloride in 300 ml of THF. The clear solution was treated with 8.45 g of 2-methylimidazole in one portion and allowed to stir overnight at room temperature. The reaction mixture was concentrated at reduced pressure to an oily residue. The residue was dissolved in 250 ml water, sodium chloride was added and the solution extracted with five 100 ml portions of ethyl acetate. The extracts were combined, washed with brine, dried (Na$_2$SO$_4$) and concentrated on a rotary evaporator to give 10.0 g of ivory colored product. Recrystallization from ethyl acetate-hexane have 5.57 g in two crops of 1-(4-imidazolylsulfonyl)-2-methylimidazole with mp 158°–9°, $\lambda_{max}^{nujol}$ 3.22 (NH), 7.30 (SO$_2$N) and 8.48 μ (SO$_2$N). NMR (DMSO, d$_6$) 520–650 Hz, m, 1H; 499 Hz, d J ~ 1 Hz, 1H; 481 Hz, d, J ~ 1 Hz, 1H (AB pattern); 450 H, d, J = 1 Hz, 1H; 425 Hz, d, J = 1 Hz, 1H (AB pattern); 154 Hz, s, 3H.

Anal. Calcd for C$_7$H$_8$N$_4$SO$_2$: C, 39.61; H, 3.80; N, 26.40. Found: C, 39.64, H, 3.88, N, 26.66.

EXAMPLE 3

1-(4-IMIDAZOLYLSULFONYL)-2-ETHYL-4-METHYLIMIDAZOLE $R^1 = R^4 = R^5 = R^6 = H$
$R^2 = C_2H_5$
$R^3 = CH_3$

A dry round bottom flask equipped with a magnetic stirrer, reflux condenser and nitrogen inlet was charged with 8.35 g of imidazole-4-sulfonylchloride and 180 ml of THF. The stirred solution was treated with 11.10 g of 2-ethyl-4-methylimidazole in one portion and stirred at room temperature overnight. The resulting precipitate was filtered off and the filtrate concentrated at reduced pressure to a foam. The foam was dissolved in ethyl acetate and the filtered solids partitioned between water and ethyl acetate. The combined organic layers were washed with water, dried with $Na_2SO_4$ and concentrated to give a waxy solid. Recrystallization was carried out using ethyl acetate and a small amount of hexane to give 8.13 g of 1-(4-imidazolylsulfonyl)-2-ethyl-4-methylimidazole, mp 147°–8°, which recrystallized to mp 149°–50°, $\lambda_{max}^{nujol}$ 3.26 (NH), 7.30 ($SO_2N$) and 8.68 $\mu$ ($SO_2N$). NMR (DMSO, $d_6$) 466 Hz, d, J = 2 Hz, 1H; 450 Hz, d, J = 2 Hz, 1H; 403 Hz, q, J = Hz, 1H; 170 Hz, q, J ~ 7.5 Hz, 2H; 116 Hz, d, J = 1 Hz, 3H; 66 Hz, t, J ~ 7.5 Hz, 3H.

Anal. Calcd. for $C_9H_{12}N_4SO_2$: C, 45.00; H, 5.04; N, 23.23. Found: C, 44.93; H, 5.09; N, 23.23.

EXAMPLE 4

1-(4-IMIDAZOLYLSULFONYL)-2-ETHYLIMIDAZOLE $R^1 = R^3 = R^4 = R^5 = R^6 = H$
$R^2 = C_2H_5$

A dry round bottom flask with a magnetic stirrer, reflux condenser and nitrogen inlet was charged with 10.85 g of imidazole-4-sulfonyl chloride and 180 ml of THF. The solution was treated with 13.4 g of 2-ethylimidazole in one portion and stirred 16 hours at room temperature. No precipitate formed during this period. The reaction mixture was refluxed 48 hours. The solvent was then removed under reduced pressure giving a clear oil. The oil was dissolved in 150 ml water and extracted three times with ethyl acetate. The extracts were washed with water, dried ($Na_2SO_4$) and concentrated to give the crude, solid product. Recrystallization from ethyl acetate-hexane gave 12.74 g of white crystals with mp 128.5°–130° which was recrystallization from ethanol to give an analytical sample of 1-(4-imidazolylsulfonyl)-2-ethylimidazole, $\lambda_{max}^{nujol}$ 3.20 (NH), 7.26 ($SO_2N$) and 8.40 $\mu$ ($SO_2N$). NMR (DMSO, $d_6$) 491 Hz, d, J = 1.5 Hz, 1H; 474 Hz, d, 5 = 1.5 Hz, 1H; 443 Hz, d, J = 2 Hz, 1H; 411 Hz, d, J = 2 Hz, 1H, 173 Hz, q, J = 7 Hz, 2H; 68 Hz, t, J = 7 Hz, 3H.

EXAMPLE 5

1-(4-IMIDAZOLYLSULFONYL)-2-n-PROPYLIMIDAZOLE $R^1 = R^3 = R^4 = R^5 = R^6 = H$
$R^2 = n\text{-}C_3H_7$ A round bottom flask equipped with a magnetic stirrer, reflux condenser and nitrogen inlet was charged with 10.85 g of imidazole-4-sulfonylchloride and 180 ml of THF. This solution was treated with a solution of 15.4 g 2-n-propylimidazole in 100 ml of THF. The reaction mixture was stirred at room temperature overnight and then refluxed 48 hours. The clear solution was concentrated to an oil and dissolved in water. The opaque solution deposited crystals on standing which were filtered, washed and dried. Recrystallization from ethyl acetate gave 10.61 g of white crystals of 1-(4-imidazolylsulfonyl)-2-n-propylimidazole with mp 163°–4°, $\lambda_{max}^{nujol}$ 3.18 (NH), 7.32 ($SO_2N$) and 8.52 $\mu$ ($SO_2N$). NMR (DMSO, $d_6$): 660–730 Hz, m, 1H; 496 Hz, d, J = 1.5 Hz, 1H; 477 Hz, d, J = 1.5 Hz, 1H; 447 Hz, d, J = 2 Hz, 1H; 415 Hz, d, J = 2 Hz, 1H; 174 Hz, t, J = 7 Hz, 2H; 82–118 Hz, sextet, J = 7 Hz, 2H; 51 Hz, t, J = 7 Hz, 3H.

EXAMPLE 6

1-(4-IMIDAZOLYLSULFONYL)-4-PHENYLIMIDAZOLE $R^1 = R^2 = R^4 = R^5 = R^6 = H$
$R^3 = C_6H_5$

A round bottom flask equipped with a magnetic stirrer, reflux condenser and nitrogen inlet was charged with 8.35 g of imidazole-4-sulfonylchloride and 300 ml or THF. The solution was treated with 14.5 g of 4-phenylimidazole in one portion and the resulting solution stirred 18 hours at room temperature. The precipitate was filtered and the filtrate concentrated at reduced pressure. The solids were triturated with water, filtered, rinsed and dried at high vacuum over NaOH; then dissolved in hot ethyl acetate, treated with charcoal, filtered and concentrated to 600 ml. Hexane was added and induced crystallization. The product was filtered, rinsed and dried giving 12.02 g of white crystals in two crops of 1-(4-imidazolylsulfonyl)-4-phenylimidazole, mp 204.5–206; $\lambda_{max}^{nujol}$ 3.13 (NH), 7.27 ($SO_2N$) and 8.61 $\mu$ ($SO_2N$). NMR (DMSO, $d_6$) 750–840 Hz, m, 1H; 495 Hz, t, J = 1Hz, 2H; 466–484 Hz, m, 4 H; 435–438 Hz, m, 3H.

EXAMPLE 7

1-(4-IMIDAZOLYLSULFONYL)-2-ISO-PROPYLIMIDAZOLE $R^1 = R^3 = R^4 = R^5 = R^6 = H$
$R^2 = i\text{-}C_3H_7$ A round bottom flask equipped with a magnetic stirrer, reflux condenser and nitrogen inlet was charged with 8.35 g of imidazole-4-sulfonylchloride and 150 ml of THF. This solution was treated with 11.10 g of 2-isopropylimidazole in one portion and the solution stirred 24 hours at room temperature. The solution was concentrated to a clear oil and partitioned between ethylacetate and water. The organic layer was washed with water and the water washes back extracted with ethyl acetate. The organic layer was dried ($Na_2SO_4$) and concentrated to a foam. The foam was dissolved in acetone and chromatographed on activity III alumina to separate 1-(4-imidazolylsulfonyl)-2-isopropylimidazole, mp 118°–120°.

EXAMPLE 8

1-(4-IMIDAZOLYLSULFONYL)-2-METHYLIMIDAZOLE HYDROCHLORIDE $R^1 = R^3 = R^4 = R^5 = R^6 = H$
$R^2 = CH_3$

A solution of 2.12 g of 1-(4-imidazolesulfonyl)-2-methylimidazole from Example 2 was dissolved in 100 ml of absolute ethanol in a dry flask equipped with a drying tube. A 50 ml aliquot of saturated ethereal hydrogen chloride was added over a five minute period. No precipitate formed immediately but did after about 15 minutes. The mixture was chilled in an ice bath for an additional 30 minutes and the precipitate filtered under a nitrogen atmosphere and dried under vacuum. The yield of white crystals of the hydrochloride of 1-(4-imidazolylsulfonyl)-2-methylimidazole was 1.87 g with mp 195°–8°. An analytical sample was made by recrystallization from ethanol and ether mixture, $\lambda_{max}^{nujol}$ 3.15–4.1 ($NR_3^+Cl^-$), 7.20 ($SO_2N$) and 8.52 $\mu$ ($SO_2N$).

Anal. Calcd for C₇H₈N₄SO₂.HCL; C, 33.78; H, 3.65; N, 22.50. Found: C, 33.67, 33.63; H; 3.70, 3.70; N, 21.68, 21.92.

The compounds of Tables I and II are obtained by use of appropriate imidazoles according to the procedure of the preceding examples.

TABLE I

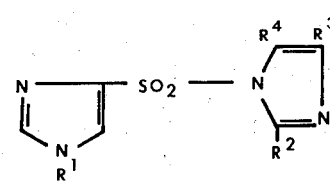

| Example | R¹ | R² | R³ | R⁴ | mp°C |
|---|---|---|---|---|---|
| 9 | H | n—C₄H₉ | H | H | 112–114 |
| 10 | H | i—C₄H₉ | H | H | 112–114 |
| 11 | H | H | CH₃ | H | 214–216 |
| 12 | H | H | n—C₃H₇ | H | 126–7 |
| 13 | H | H | i—C₃H₇ | H | 151–2 |
| 14 | H | H | o—C₆H₄CH₃ | H | 180–1.5 |
| 15 | H | CH₃ | C₆H₅ | H | 165–7 |
| 16 | H | C₂H₅ | C₆H₅ | H | 130–2 |
| 17 | H | H | CH₃ | CH₃ | 235 dec |
| 18 | H | H | C₆H₅ | CH₃ | 177.5–9.5 |
| 19 | H | H | C₆H₅ | C₂H₅ | 145–7 |
| 20 | H | H | —CH₂CH₂CH₂CH₂— |  | 257 dec |
| 21 | H | H | —CH₂CH₂C=C— (fused benzene) |  | 238 dec |
| 22 | H | H | —CH=CH—C=C— (fused benzene) |  | 250 dec |
| 23 | H | SCH₃ | H | H | 172–3.5 |
| 24 | H | SC₂H₅ | H | H | 174.5–5.5 |
| 25 | H | H | CH₂CN | H | 169–170.5 |
| 26 | H | H | p—C₆H₄F | H | 221–3 |
| 27 | H | H | o—C₆H₄F | H | 214–6 |
| 28 | H | H | o—C₆H₄Cl | H | 215–6 |
| 29 | H | SCH₃ | C₆H₅ | H | 179–180.5 |
| 30 | C(O)—NHCH₃ | H | C₆H₅ | H | 214–215.5 |
| 31 | H | nC₁₇H₃₅ | H | H | 112–114 |
| 32 | H | CH₂C₆H₅ | H | H | 154–155.5 |
| 33 | H | SOCH₃ | H | H | 157–158.5 |
| 34 | H | H | naphthyl | H | 214–15.5 |
| 35 | H | H | C₆H₁₁ | H | 92–94° |
| 36 | H | H | t—C₄H₉ | H | 202–6 |
| 37 | H | H | CH₂CH₂NHCOCF₃ | H | 183–4 |
| 38 | H | H | p—C₆H₄Cl | H | 247.5–248.5 |
| 39 | H | H | p—C₆H₄NH₂ | H | 213–216 |
| 40 | H | H | m—C₆H₄OCH₃ | H | 173–4 |
| 41 | H | H | p—C₆H₄OCH₃ | H |  |
| 42 | H | H | p—C₆H₄NO₂ | H | 257–9 (dec.) |
| 43 | H | H | 2,4—C₆H₃(CH₃)₂ | H | 175.5–77 |
| 44 | H | H | p—C₆H₄—C₆H₅ | H | 270–72 |
| 45 | H | H | C(O)—NC₆H₅ | H | 235 (dec.) |
| 46 | H | H | CH₂CO₂CH₃ | H | 135–9 |
| 47 | H | H | p—C₆H₄CH₃ | H | 212–13 |
| 48 | H | CH₃ | p—C₆H₅Cl | H | 236–9 |
| 49 | H | CH₃ | C₆H₅ | H | 165–7 |
| 50 | H | C₂H₅ | C₆H₅ | H | 130–2 |
| 51 | H | C₃H₇ | C₆H₅ | H | 134–6 |
| 52 | H | SCH₃ | C₆H₅ | H | 179–180.5 |
| 53 | H | SC₂H₅ | C₆H₅ | H | 111–113 |
| 54 | H | H | nC₃H₇ | nC₃H₇ | 135–136.5 |
| 55 | H | H | C₆H₅ | CH₃ | 177.5–179.5 |
| 56 | H | H | C₆H₅ | C₂H₅ | 145–7 |
| 57 | H | H | C₆H₅ | iC₃H₇ | 195.5–8 |
| 58 | H | H | C₆H₅ | C₆H₅ | 223–5 |
| 59 | CH₃ | H | C₆H₅ | H | 217–8 |
| 60 | CH₃ | nC₃H₇ | H | H | 72–3 |
| 61 | CH₃ | H | C₆H₅ | CH₃ | 151–3 |
| 62 | CH₃ | H | CH₃ | CH₃ | 107–110 |
| 63 | CH₃ | SCH₃ | C₆H₅ | CH₃ | 144–145.5 |
| 64 | CH₃ | CH₃ | —CH=CH—CH=CH— |  |  |
| 65 | H | nC₃H₇ | —CH=CH—CH=CH— |  | 159–162 |
| 66 | H | nC₇H₁₅ | H | H | 88–91 |
| 67 | H | H | CH=CHCO₂CH₃ | H | 166–9 |
| 68 | H | H | CH₂CH₂CO₂CH₃ | H | oil |

TABLE I-continued

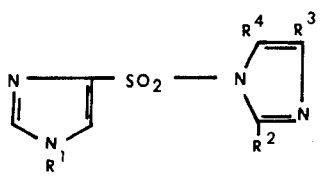

| Example | R¹ | R² | R³ | R⁴ | mp°C |
|---|---|---|---|---|---|
| 69 | H | CH₂CH₂C₆H₅ | H | H | 110–12 |
| 70 | H | H | β—C₁₀H₇ | H | 214–215.5 |
| 71 | H | H | C₆H₁₁ | H | 92–94 |

TABLE II

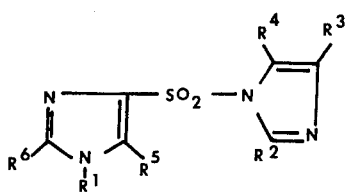

| Example | R¹ | R² | R³ | R⁴ | R⁵ | R⁶ | mp°C |
|---|---|---|---|---|---|---|---|
| 72 | H | H | C₆H₅ | H | H | CH₃ | 224–6 |
| 73 | H | H | CH₂CN | H | H | H | 195–6 |
| 74 | H | H | —CH₂CH₂C=C— | | H | H | 250 dec. |
| 75 | H | H | H | H | H | H | |
| 76 | H | nC₃H₇ | H | H | H | CH₃ | 128–130.5 |

The compounds of Table III are obtained by reacting 4-imidazolylsulfonyl chloride with an amino compound of the formula HNR⁷R⁸ according to the procedure of prior examples.

Compounds where R' is hydrogen can be reacted to replace the hydrogen with alkyl, acyl or related groups. As an illustration the compound of Example 131 was prepared as follows:

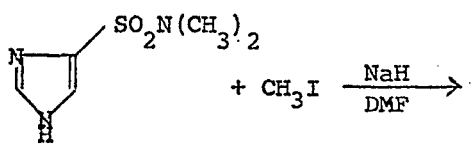

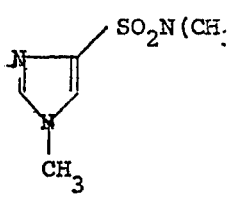

The hexane-washed NaH (2.16 g) was slurried in 75 ml of DMF and chilled to 0° in an ice bath. The imidazole sulfonamide (8.75 g) was added portionwise with a nitrogen atmosphere and allowed to stir one hour without the ice bath. After replacing the ice bath, 7.8 g of methyl iodide was added slowly and the mixture was allowed to stir at 25° for 18 hours. After pouring into 500 ml of water, the product was extracted with EtOAc giving a pale yellow oil, 2.05 g. Continuous extraction with EtOAc for 60 hours gave 5.50 g of oil which solidified on standing after concentration. The ir spectra of both materials were identical. A small aliquot of both samples were crystallized from benzene giving identical material by mp 117°–9° and ir spectra. Recrystallization of entire sample from benzene after charcoal treatment gave 4.74 g with mp 118°–20°. The NMR (DMSO, d₆): 479 Hz, s, 2H; 227 Hz, s, 3H; 162 Hz, s, 6H.

In a similar manner, use of N-β-chloroethylmorpholine, gave the compound of Example 132. The use of (CH₃)₂NCOCl and benzoyl chloride gave products of Examples 114–118 and 121, while cyclopropyl carbonyl chloride gave the compounds of Examples 122–3. Trityl chloride and phenacyl bromide gave the compounds of Examples 133 and 120 when hexamethylphosphoramide (HMPA) was used as solvent in place of DMF. Phenacyl bromide with K₂CO₃ in acetone was used for the compound of Example 119.

TABLE III
4-Imidazolylsulfonamides of Primary and Secondary Amines
| Example | R¹ | X | mp °C |
|---|---|---|---|
| 77 | H | NHCH$_3$ | 157–8 |
| 78 | H | N(CH$_3$)$_2$ | 238–40 |
| 79 | H | NHCH$_2$CN | 167–8 |
| 80 | H | N(CH$_2$CH=CH$_2$)$_2$ | 184–6 |
| 81 | H | N(CH$_3$)OCH$_3$ | 200–1 |
| 82 | H | NHCO$_2$C$_2$H$_5$ | 183–5 |
| 83 | H | NHCH(CH$_2$)(CH$_2$) | 178–9 |
| 84 | H | N(CH$_3$)C$_6$H$_5$ | 152–3 |
| 85 | H | N(C$_2$H$_5$)CH$_2$C$_6$H$_5$ | 139–40 |
| 86 | H | NHCH$_2$C$_6$H$_5$ | 185–7 |
| 87 | H | NHC$_6$H$_4$CH$_3$(p) | 230–2 |
| 88 | H | NHC$_6$H$_4$COCH$_3$(p) | 285–7 |
| 89 | H | NHC$_6$H$_4$CN(p) | 297–8 |
| 90 | H | morpholino | 235–7 |
| 91 | H | 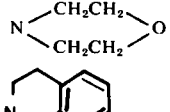 | 255–6d |
| 92 | H | 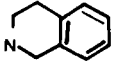 | 191–3 |
| 93 | H | —N(CH$_2$)$_6$ | 221–3 |
| 94 | H | 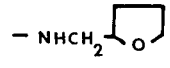 | 222–3 |
| 95 | H | 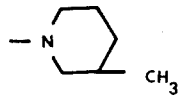 | 237–9 |
| 96 | H | 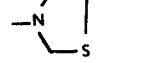 | 227–8 |
| 97 | H | 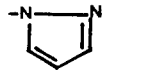 | 253–4 |
| 98 | H | 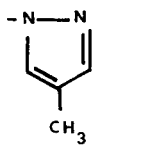 | 200–1 |
| 99 | H | 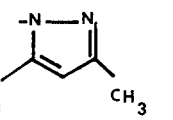 | 208–10 |

TABLE III-continued
4-Imidazolylsulfonamides of Primary and Secondary Amines

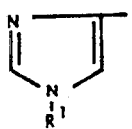 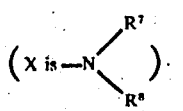

| Example | R¹ | X | mp °C |
|---|---|---|---|
| 100 | H | -N(triazolyl) | 243.5–45 |
| 101 | H | -NH-C(C₆H₅)=N-N= (pyrazolyl) | 228–9 |
| 102 | H | N(C₂H₅)C₆H₅ | 121–3 |
| 103 | H | N(CH₃)CH₂C₆H₅ | 183–5 |
| 104 | H | NHCH(CH₃)C₆H₅ | 152–4 |
| 105 | H | N(CH₃)CH₂CH₂C₆H₅ | 147–8 |
| 106 | H | NH-(3-pyridyl) | 251–4 |
| 107 | H | NHCH₂-(2-pyridyl) | 191–3 |
| 108 | H | NH(CH₂)₃C₆H₅ | 131–6 |
| 109 | H | N(1,2,3,6-tetrahydropyridyl)-C₆H₅ | 257–8 |
| 110 | H | N(piperidyl)-C₆H₅ | 299–302 |
| 111 | H | NH-(6-methoxy-3-pyridyl) | 203.5–6 |
| 112 | H | NHCH₂CH₂N(imidazolidinon-2-yl) | 208–11 |
| 113 | H | NH-(1-phenyl-2,3-dimethyl-5-pyrazolon-4-yl) | 300–2 |
| 114 | O=C-N(CH₃)₂ | N(CH₃)₂ | 123–4.5 |
| 115 | O=C-N(CH₃)₂ | N(CH₃)C₆H₅ | 123–5 |
| 116 | O=C-N(CH₃)₂ | N(morpholino) | 179.5–81.5 |
| 117 | O=C-N(CH₃)₂ | N(CH₂CH=CH₂)₂ | oil bp 190/0.03 |

TABLE III-continued
4-Imidazolylsulfonamides of Primary and Secondary Amines

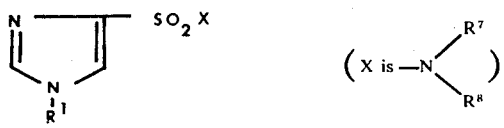

| Example | R¹ | X | mp °C |
|---|---|---|---|
| 118 | COC$_6$H$_5$ | N(CH$_2$CH=CH$_2$)$_2$ | 106–8 |
| 119 | COC$_6$H$_5$ | NO (morpholino) | 188–9 |
| 120 | COC$_6$H$_5$ | N(CH$_3$)$_2$ | 146–7.5 |
| 121 | COC$_6$H$_5$ | N(CH$_3$)C$_6$H$_5$ | 117–18.5 |
| 122 | CO-cyclopropyl | | 112–4 |
| | | N(CH$_3$)$_2$ | |
| 123 | CO-cyclopropyl | NO (morpholino) | 132–4 |
| 124 | H | imidazolyl-SC$_2$H$_5$ | 209–10 |
| 125 | H | –NH–(triazole ring with NH, N=, NH) | 228–9d |
| 126 | H | NHC(=NH)NHC$_6$H$_5$ · HCl | 272d |
| 127 | H | NH–(thiadiazole)–SCH$_3$ | 176–7d |
| 128 | CH$_3$ | N(CH$_3$)C$_6$H$_5$ | 113–5 |
| 129 | CH$_3$ | N(CH$_2$CH=CH$_2$)$_2$ | 45–7 |
| 130 | CH$_3$ | NO (morpholino) | 149.5–50.5 |
| 131 | CH$_3$ | N(CH$_3$)$_2$ | 118–20 |
| 132 | CH$_2$CH$_2$NO | NHCH$_2$CH$_2$NO | 121–3 |
| 133 | C(C$_6$H$_5$)$_3$ | N(CH$_3$)$_2$ | 179–82 |
| 134 | CH$_2$COC$_6$H$_5$ | N(CH$_3$)$_2$ | 167–9 |
| 135 | CH$_2$COC$_6$H$_5$ | NO (morpholino) | 206–8 |
| 136 | CH$_2$CHOHC$_6$H$_5$ | N(CH$_3$)$_2$ | 135–6 |
| 137 | CH$_2$C(OO)C$_6$H$_5$ (ketal) | NO (morpholino) | 161–3 |
| 138 | CH$_2$CH=CH$_2$ | N(CH$_3$)C$_6$H$_5$ | oil |
| 139 | H | N=N (with SCH$_3$) | 206–8.5 |

The compound of Example 140 is prepared by reacting 1 part of 4-imidazolylsulfonyl chloride with about 10 parts of liquid ammonia, Ammonia is distilled off the mixture and the sulfonamide purified by recrystallization from water. The other compounds of Table IV where R' is other than hydrogen, are prepared by reacting the compound of Example 140 with appropriate reagents. For example, use of 2-bromoethylbenzene and 2,5-dimethyl benzyl chloride gives the compounds of Examples 142 and 146 respectively.

TABLE IV

4-Imidazolylsulfonamides

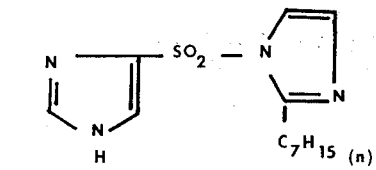

| Example | R¹ | mp °C |
|---|---|---|
| 140 | H | 237–8 |
| 141 | CH₂CH₂-N(cyclohexyl-N ring) | 142.5–44 |
| 142 | CH₂CH₂C₆H₅ | 159.5–61 |
| 143 | CH₂C₆H₄Cl(p) | 152–4 |
| 144 | CH₂C₆H₄CH₃(p) | 135–7 |
| 145 | CH₂C₆H₅ | 168–9.5 |
| 146 | CH₂C₆H₃(CH₃)₂ (2,5) | 175–7 |

In addition to the products characterized in the preceding specific examples, other compounds within the scope of this invention include the following: 4-allyl-1-(4-imidazolylsulfonyl)-5-methylimidazole, 2-benzyl-1-(4-imidazolylsulfonyl)-4-methyl-5-phenylimidazole, 4,5-bis(p-methylphenyl)-1-(4-imidazolylsulfonyl)imidazole, 4,5-diphenyl-(4-imidazolylsulfonyl)-2-isopropylimidazole, and 2-cyclopropyl-1-(4-imidazolylsulfonyl)imidazole.

As previously mentioned, these 1-(4-imidazolylsulfonyl)imidazoles can be alkylated or acylated by use of a hydrocarbyl halide, acyl or aroyl halide of an alkanoic or aromatic hydrocarbyl acid (wherein the hydrocarbyl is generally of up to 7 carbons) or an alkylene oxide to give hydroxyalkyl of generally 2 to 3 carbons. For example, with methyl iodide, n-amyl bromide, benzyl bromide, propionyl chloride and benzoyl chloride in the presence of sodium hydride and inert diluent with 1-(4-imidazolylsulfonyl)imidazole give 1-(1-methyl-4-imidazolylsulfonyl)imidazole, 1-(1-n-amyl-4-imidazolylsulfonyl)imidazole, 1-(1-benzyl-4-imidazolylsulfonyl)imidazole, 1-(1-propionyl-4-imidazolylsulfonyl)imidazole, and 1-(1-benzoyl-4-imidazolylsulfonyl)imidazole. When 1-(4-imidazolylsulfonyl)imidazole is reacted with alkylene oxide such as ethylene oxide or propylene oxide, there is obtained the corresponding hydroxy alkyl derivative, e.g., 1-(1-β-hydroxyethyl-4-imidazolylsulfonyl)imidazole or 1-(1-β-hydroxypropyl-4-imidazolyl)imidazole.

Treatment of cotton with 4-imidazolesulfonyl chloride in t-butyl alcohol in the presence of a catalytic amount of triethyl amine on a steam bath for several hours followed by air drying with or without a water wash imparts flame retardant properties to the cotton without discoloration or undue loss of esthetics. Thus a ball of untreated cotton immediately ignites when contacted with a match flame and continues to burn until only a faint ash remains whereas a treated cotton ball will char on the surface when contacted with an open flame but will not continue to burn even with repeated contact with an open flame. It is self-extinguishing.

The effectiveness of the new 4-imidazolylsulfonamides of this invention as plasticizers is shown as follows: To a 2 ml portion of a 10% solution of polyvinyl chloride in tetrahydrofuran was added 0.1 g of representative compounds. After solution of the 4-imidazolylsulfonamide was complete, the mixture was cast on a glass plate and the solvent evaporated. The following representative compounds showed good plasticization properties i.e., flexible films that were generally clear and soft as compared to a control which was much harder and stiffer.

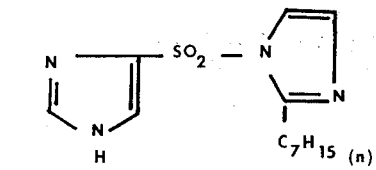

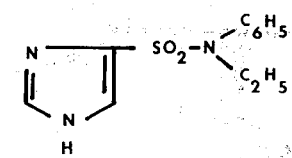

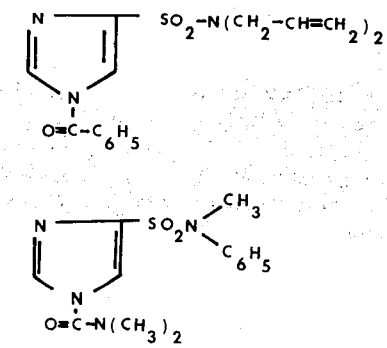

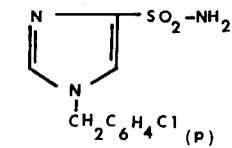

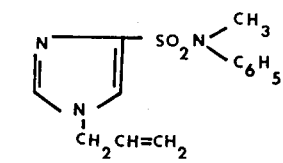

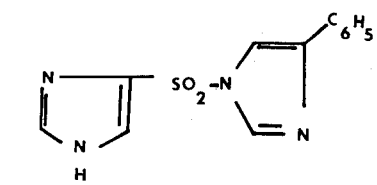

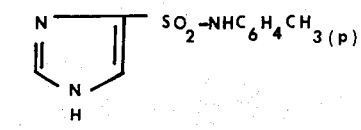

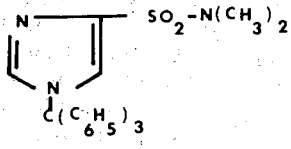

What is claimed is:
1. A compound of the formula

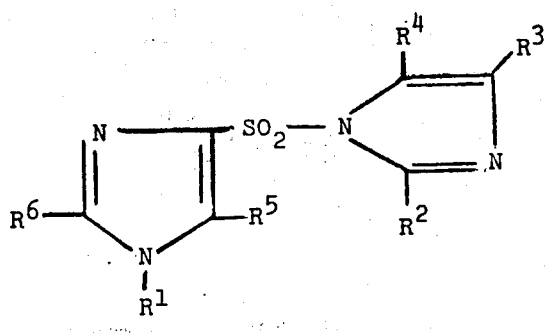

wherein
R$^1$ is selected from the group consisting of H, alkyl of 1–3 carbons, alkenyl of 3 carbons, aminocarbonyl, methylaminocarbonyl, dimethylaminocarbonyl, benzoyl, aralkyl of 7 to 19 carbons, alkanoyl of up to 7 carbons, benzoylmethyl or cycloalkanoyl of 4 carbons;

R$^2$, R$^3$ and R$^4$ are individually selected from the group consisting of H, alkyl of up to 17 carbons; cycloalkyl of up to 6 carbons, aryl of 6–12 carbons substituted with up to two halo, nitro, amino, methoxy or alkyl groups having up to 3 carbons; alkenyl of 3 carbons; carbalkoxyalkyl and carbalkoxyalkenyl of 3–4 carbons; and thioalkyl of 1–2 carbons;

with the proviso that R$^3$ and R$^4$ together can be a divalent hydrocarbyl group of 4 chain carbons and having a total of from 4 to 8 carbons; and R$^5$ and R$^6$ individually are H or alkyl of 1–3 carbons.

2. A compound of claim 1 where R$^2$, R$^3$ and R$^4$ are alkyl of 1–4 carbons.

3. The compound of claim 1 in which all the R groups are H; 1-(4-imidazolylsulfonyl)imidazole.

4. The compound of claim 1 in which R$^1$, R$^3$, R$^4$, R$^5$ and R$^6$ are each H and R$^2$ is methyl; 1-(4-imidazolylsulfonyl)-2-methylimidazole.

5. The compound of claim 1 in which R$^1$, R$^4$, R$^5$ and R$^6$ are each H, R$^2$ is ethyl and R$^3$ is methyl; 1-(4-imidazolylsulfonyl)-2-ethyl-4-methylimidazole.

6. The compound of claim 1 in which R$^1$, R$^3$, R$^4$ R$^5$ and R$^6$ are each H and R$^2$ is ethyl; 1-(4-imidazolylsulfonyl)-2-ethylimidazole.

7. The compound of claim 1 in which R$^1$, R$^3$, R$^4$, R$^5$ and R$^6$ are each H and R$^2$ is propyl; 1-(4-imidazolylsulfonyl)-2-propylimidazole.

8. The compound of claim 1 in which R$^1$, R$^2$, R$^4$, R$^5$ and R$^6$ are each H and R$^3$ is phenyl; 1-(4-imidazolylsulfonyl)-4-phenylimidazole.

* * * * *

UNITED STATES PATENT OFFICE
CERTIFICATE OF CORRECTION

PATENT NO. : 3,932,444
DATED : January 13, 1976
INVENTOR(S) : Richard Lee Ellis

It is certified that error appears in the above-identified patent and that said Letters Patent are hereby corrected as shown below:

Col. 2, line 15 - before "carbons" insert --each of 3-4--;

Col. 6, line 11 - "or" should be --of--;

Col. 9, line 60 - "N(CH" should be --N(CH$_3$)$_2$--;

Col. 11, Ex. 83 - "CH⟨CH$_2$/CH$_2$⟩" should be --CH⟨CH$_2$|CH$_2$⟩--;

Col. 15, Ex. 139 - "N=N / SCH$_3$" should be --N—N / SCH$_3$--.

Signed and Sealed this eighteenth Day of May 1976

[SEAL]

Attest:

RUTH C. MASON
*Attesting Officer*

C. MARSHALL DANN
*Commissioner of Patents and Trademarks*